United States Patent [19]

Linder

[11] 4,185,639

[45] Jan. 29, 1980

[54] ADJUSTABLE STOP FOR ENDOTRACHEAL TUBE GUIDE

[76] Inventor: Gerald S. Linder, 16693 Charmel La., Pacific Palisades, Calif. 90272

[21] Appl. No.: 890,401

[22] Filed: Mar. 27, 1978

[51] Int. Cl.² .......................................... A61M 25/00
[52] U.S. Cl. ........................ 128/200.26; 128/DIG. 26
[58] Field of Search ............... 128/351, 350 R, 349 R, 128/348, 343, 341, DIG. 26; 24/129 D, 238; 403/362, 373, 374, 367, 389–391; 151/21 C, 23

[56] References Cited

U.S. PATENT DOCUMENTS

| 3,460,541 | 8/1969 | Doherty | 128/351 |
| 3,957,055 | 5/1976 | Linder et al. | 128/351 |
| 4,114,626 | 9/1978 | Beran | 128/DIG. 26 |

*Primary Examiner*—Stephen C. Pellegrino
*Attorney, Agent, or Firm*—B. F. Spencer

[57] ABSTRACT

An adjustable stop is disclosed for use with endotracheal tube or catheter guides for setting the depth of penetration of the distal end of the guide into the endotracheal tube or catheter. The adjustable stop is composed of a body of resilient material having a central bore extending completely through the body. A surface portion of the body is provided for abutment against the opening to the endotracheal tube or catheter. At least one hole, laterally displaced from the central bore, extends partially into the resilient body from the rear surface. The guide is inserted into the adjustable stop through the central bore, and the stop is manually positioned along the length of the guide with respect to its distal end to set the desired depth of penetration. The proximal end portion of the guide is formed into a suitable handle and the end is manually inserted into the laterally displaced hole. The forced insertion of the proximal end of the guide into the laterally displaced hole provides a secure anchor for the handle while producing a clamping and locking force upon the surface of the guide by stretching the walls of the resilient body surrounding the bore.

11 Claims, 5 Drawing Figures

ADJUSTABLE STOP FOR ENDOTRACHEAL TUBE GUIDE

BACKGROUND OF THE INVENTION

The present invention relates to endotracheal tube or catheter guides, and in particular to adjustable stops for use with such guides to set the depth of penetration of the guide into the endotracheal tube or catheter.

A variety of guides and stylets are available for use with flexible endotracheal tubes and catheters to aid the physician in intubating such instruments with a minimum of trauma to the patient. The guide or stylet is usually inserted within the endotracheal tube or catheter before intubation into the patient. After intubation, the guide or stylet is carefully withdrawn.

Of considerable importance to the physician is the ease by which the guide can be configured along with the endotracheal tube or catheter into a semi-permanent shape best suited for intubation; the necessity for adjustably setting and permanently maintaining the depth of penetration of the distal end of the guide within the tube or catheter; and the ease with which the guide can be withdrawn from the tube or catheter after intubation.

One type of stylet or guide in wide use consists of a long thin wire of maleable metal, such as soft iron, copper, or aluminum, which has been completely encapsulated and hermetically sealed with a tough layer of elastomeric polymer, such as nylon, polyolefin, polypropylene, or the like. While such guides have been relatively easy to configure into a desired shape and can be withdrawn from an intubated endotracheal tube or catheter without difficulty, some problems have been encountered in setting and maintaining a predetermined depth of penetration of the guide into the tube or catheter.

One method employed to preset the depth of penetration has been to form a right-angle or ninety-degree bend near the proximal end of the guide for abutment against one side of the opening to the endotracheal tube or catheter. Another method has been to form a small closed or circular loop with the proximal end of the guide with a portion of the loop abutting the open end of the endotracheal tube or catheter. Neither of these methods has been found to be completely satisfactory, nor do they offer any satisfactory way by which the physician can grasp the proximal end portion of the guide or stylet for manipulation without the risk of accidentally rebending or altering the shape of the proximal end, thereby causing the distal end to dangerously penetrate beyond minimum safe limits.

To alleviate this serious problem, an improved endotracheal tube stylet has been introduced employing an adjustable stop of tough synthetic rubber mounted upon and slidable along the length of the stylet for setting the desired depth of penetration. A description of this new stylet appears in the March-April 1974 issue of *Journal of the International Anesthesia Research Society*, Vol. 53, No. 2, pages 341-342.

A further solution to the above-mentioned problems appears in U.S. Pat. No. 3,957,055, wherein an adjustable stop has been described which performs not only the function of setting and maintaining the desired preset depth of penetration but also serves the additional function of providing an anchor for the proximal end of the guide, thereby enabling the proximal end portion of the guide to be formed into a convenient and useful handle. The present invention is concerned with further improvements in adjustable stops for use with endotracheal tube or catheter guides to overcome the above-mentioned problems.

DESCRIPTION OF THE INVENTION

Figure 1:
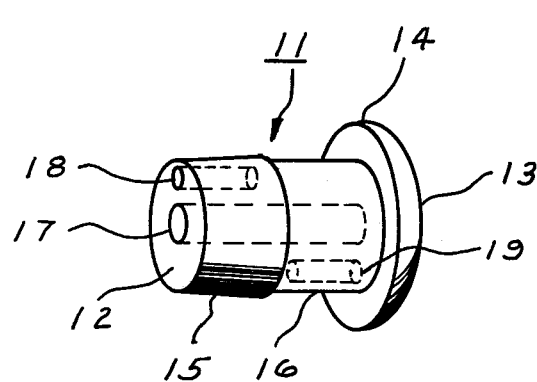
FIG. 1 is a perspective view of the preferred embodiment of the invention.

Referring to FIG. 1, a cylindrically-shaped body 11 of resilient polymer material, such as natural or synthetic rubber, polyvinyl chloride, or the like, is shown having a first flat end surface 12 and a second flat end surface 13. A disk-shaped shoulder portion 14, having a diameter approximately fifty percent larger than the diameter of the cylindrical body 11, is formed at the second flat end surface 13. A portion 15 of the cylindrical body 11 adjacent the first end surface 12 is slightly tapered or cone-shaped, as shown, while the portion 16 adjacent the shoulder portion 14 is substantially straight.

A central bore 17 extends coaxially through cylindrical body 11 from end surface 12 to end surface 13. The diameter of bore 17 is sufficient to permit the adjustable stop of FIG. 1 to slide easily over the surface of an endotracheal tube guide.

In the preferred embodiment illustrated in FIG. 1, two cylindrical holes 18 and 19 extend partially into the cylindrical body 11 from end surfaces 12 and 13 respectively, as shown, and these holes 18 and 19 are approximately parallel to and laterally offset from central bore 17. The holes 18 and 19 are diametrically disposed with respect to central bore 17. By providing the two holes 18 and 19, as shown, the adjustable stop may be used in either one of two possible configurations, as will be discussed below. However, only one such hole is necessary to the invention.

The diameter of holes 18 and 19 is smaller than the outside diameter of the endotracheal tube guide for which the adjustable stop is designed to be used, and is smaller than the diameter of central bore 17. The depth of each of the holes 18 and 19 is approximately one-half the distance between end surfaces 12 and 13, as shown.

The adjustable stop of FIG. 1 may be manufactured by any suitable conventional molding process, and in one example it was composed of polyvinyl chloride having a length of approximately 1.7 centimeters between end surfaces 12 and 13 and a diameter of approximately 1.7 centimeters at shoulder portion 14. The diameters of central bore 17 and holes 18 and 19 will vary depending upon the sizes of endotracheal tube or catheter guies to be used. The diameter of cylindrical body 11 at end surface 12 and the taper or portion 15 is determined by the inside diameter of the connector used with conventional endotracheal tubes or catheters.

Figure 2:
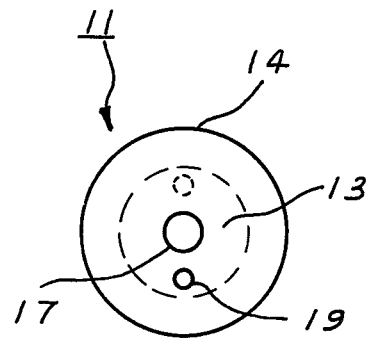
FIG. 2 is an end view of the adjustable stop invention of FIG. 1.

FIG. 2 illustrates the adjustable stop as viewed from the flat end surface 13, and better illustrates the relative diameters of central bore 17 and hole 19.

Figure 3:
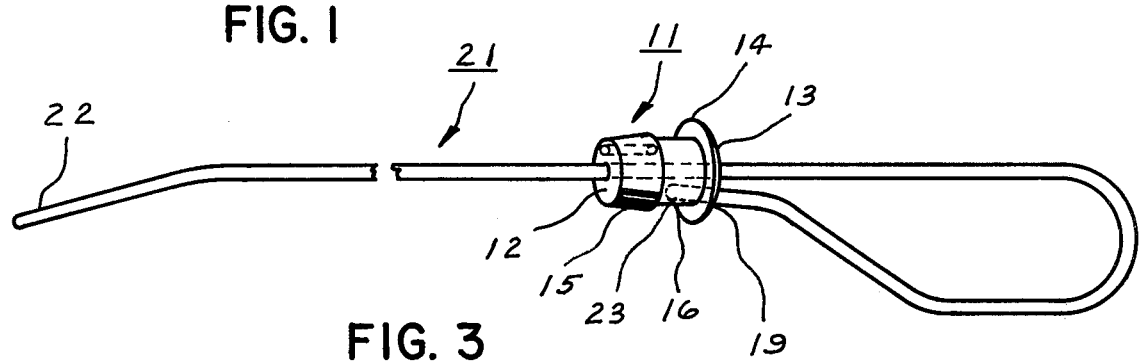
FIG. 3 is a perspective view of the invention used with an endotracheal tube or catheter guide.

FIG. 3 illustrates the adjustable stop installed and locked into position upon an endotracheal tube guide 21. The distal end 22 is illustrated with a slight bend, while the proximal end portion is shaped to form a handle in a manner somewhat similar to that disclosed in my U.S. Pat. No. 3,957,055. The tapered portion 15 of resilient cylindrical body 11 faces the distal end 22 of guide 21 and is intended to fit within the standard connector used with the endotracheal tube or catheter guide.

Figure 4:
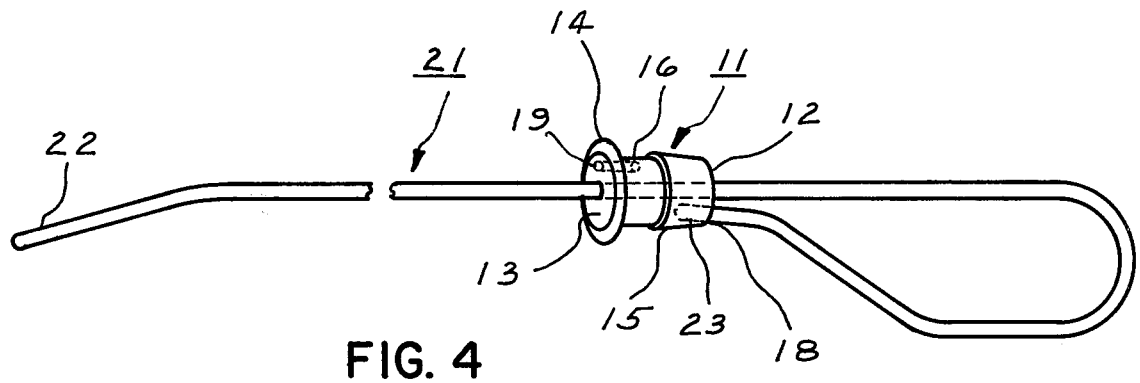
FIG. 4 is a perspective view of the adjustable stop installed in the reverse position upon the endotracheal tube or catheter guide.

After the adjustable stop has neen positioned upon the endotracheal tube guide 21 to the desired depth of penetration of the distal end 22, the stop is locked into position upon guide 21 and the proximal end 23 is rigidly secured to the adjustable stop by forced insertion of end 23 into the laterally offset hole 19. The forced insertion of proximal end 23 into the smaller diameter hole 19 securely anchors end 23 while causing a deformation in the shape of portion 16 and end surface 13 of cylindrical body 11. The change in shape of portion 16 stretches the cylindrical body 11 to cause the walls of central bore 17 to apply a clamping and holding force upon the surface of guide 21.

Where the opening to a connector used with an endotracheal tube or catheter guide is larger than the diameter of end surface 12 and tapered portion 15, tapered portion 15 and straight portion 16 will extend within the opening to the connector until shoulder portion 14 comes into contact with the mouth of the connnector, thereby limiting the depth of penetration of distal end 22.

Where the opening to an endotracheal tube or catheter is smaller than the diameter of end surface 12 of the adjustable stop, the embodiment illustrated in FIG. 4 may be used. In this version, the proximal end 23 is inserted into lateral hole 18 in the straight portion 15. The forced insertion of proximal end 23 anchors the handle and clamps the stop upon guide 21 in the same manner described above in connection with FIG. 3. Flat end surface 13 of shoulder 14 serves to limit the depth of penetration of distal end 22 upon its contact with the opening to the endotracheal tube or catheter. In this embodiment, the straight portion 16 of body 11 serves as a convenient finger grip for the physician. The preferred embodiment of the invention is, therefore, usable in a number of ways with a variety of sizes and types of endotracheal tubes and catheters.

Figure 5:
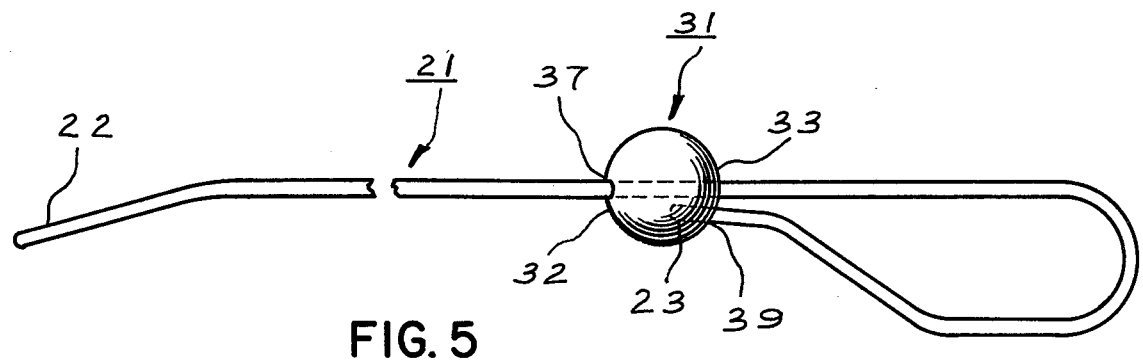
FIG. 5 is an alternative embodiment of the invention.

FIG. 5 illustrates an adjustable stop employing a resilient body 31 in the shape of a ball or sphere and having a first or front surface portion 32 and a rear or second surface portion 33. A central bore 37 extends completely through body 31 between the front and rear surfaces 32 and 33. The diameter of bore 37 is sufficient to permit the stop to slide easily over the surface of guide 21. A laterally displaced hole 39, offset from central bore 37, extends partially into body 31. The diameter of hole 39 is smaller than the diameter of the proximal end 23 of the guide 21.

The adjustable stop of FIG. 5 is installed upon guide 21 in the same manner as described above, and the forced insertion of proximal end 23 into hole 39 anchors the handle and clamps the stop upon the surface of the guide. The diameter of body 31 may be chosen to fit within a standard connector, if desired, or selected for abutment against the open end of the endotracheal tube or catheter.

The improved adjustable stop of this invention applies a strong clamping force upon the surface of the guide to hold and maintain the depth of penetration of the guide as the endotracheal tube or catheter is being intubated, and provides a secure anchor for the proximal end of the guide to form a sturdy and rigid handle.

Since many changes can be made in the above-described apparatus and many different embodiments of this invention could be made without departing from the scope thereof, it is intended that all matter contained in the above description or shown in the accompanying drawings shall be interpreted as illustrative and not in a limiting sense.

What is claimed is:

1. An adjustable stop adapted for use with an endotracheal tube guide, comprising in combination:
    (a) a cylindrical body of resilient material having first and second end surfaces;
    (b) a central bore extending coaxially through said cylindrical body between the first and second end surfaces, the diameter of said central bore being sufficient to permit the adjustable stop to slide over the surface of the endotracheal tube guide; and
    (c) at least one hole extending partially into said cylindrical body from one of the first or second end surfaces, said one hole being approximately parallel to and laterally offset from said central bore, the diameter of said one hole being smaller than the diameter of the endotracheal tube guide to permit an expansion of the resilient material about said one hole upon insertion of one end of said endotracheal tube guide therein and thereby provide a clamping force on the tube guide within said central bore.

2. The adjustable stop as defined by claim 1 wherein the first and second end surfaces of said cylindrical body are substantially flat and are perpendicular to the axis of said cylindrical body.

3. The adjustable stop as defined by claim 1 further comprising a shoulder portion formed at one of the first or second end surfaces of said cylindrical body, said shoulder portion extending radially outward from the cylindrical surface of said body.

4. The adjustable stop as defined by claim 3 wherein said shoulder portion is disk-shaped, and wherein the diameter of said disk-shaped shoulder portion is approximately fifty percent larger than the diameter of said cylindrical body.

5. The adjustable stop as defined by claim 1 further comprising an additional hole extending partially into said cylindrical body from the other of the first or second end surfaces, said additional hole being approximately parallel to and laterally offset from said central bore, the diameter of said attitional hole being smaller than the diameter of the endotracheal tube guide.

6. The adjustable stop as defined by claim 5 wherein said one hole and said additional hole are diametrically disposed with respect to said central bore.

7. The adjustable stop as defined by claim 1 wherein said cylindrical body of resilient material includes a tapered portion adjacent one of the first or second end surfaces.

8. An adjustable stop adapted for use with an endotracheal tube guide, comprising in combination:
    (a) A body of resilient material having first and second surfaces;
    (b) a central bore extending through said resilient body between the first and second surfaces, the diameter of said central bore being sufficient to permit the adjustable stop to slide over the surface of the endotracheal tube guide; and (c) a hole extending partially into said resilient body from one of the first or second surfaces, said hole being laterally offset from said central bore and having a diameter smaller than the diameter of the endotracheal tube guide to permit an expansion of the resilient material about said one hole upon insertion of one end of said endotracheal tube guide therein and thereby provide a clamping force on the tube guide within said central bore.

9. The adjustable stop as defined by claim 8 wherein said body of resilient material comprises a cylindrical section having first and second flat end surfaces.

10. The adjustable stop as defined by claim 8 further comprising an additional hole extending partially into said resilient body from the other of the first or second surfaces, said additional hole being laterally offset from said central bore and having a diameter smaller than the diameter of the endotracheal tube guide.

11. The combination comprising:

(a) a body of resilient material having first and second surfaces and a central bore extending through said body between said surfaces;

(b) an elongated endotracheal tube guide having a distal end and a proximal end, said elongated endotracheal tube guide extending through the central bore of said resilient body; and (c) means adapted for locking the position of said resilient body upon said endotracheal tube guide and securing the proximal end of said guide to said resilient body, said means including a hole extending partially into said resilient body from one of the first or second surfaces, said hole being laterally offset from said central bore and having a diameter smaller than the diameter of the proximal end of said endotracheal tube guide to permit an expansion of the resilient material about said one hole upon insertion of one end of said endotracheal tube guide therein and thereby provide a clamping force on the tube guide within said central bore.

* * * * *